(12) United States Patent
Ou et al.

(10) Patent No.: US 7,626,065 B2
(45) Date of Patent: *Dec. 1, 2009

(54) PROCESS FOR PRODUCING PARA-XYLENE

(75) Inventors: John Di-Yi Ou, Houston, TX (US);
Harold W. Helmke, Jr., Kingwood, TX (US); John R. Porter, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/196,515

(22) Filed: Aug. 22, 2008

(65) Prior Publication Data

US 2008/0306318 A1    Dec. 11, 2008

Related U.S. Application Data

(63) Continuation of application No. 11/784,981, filed on Apr. 10, 2007, now Pat. No. 7,439,412.

(60) Provisional application No. 60/794,864, filed on Apr. 25, 2006.

(51) Int. Cl.
*C07C 5/27*    (2006.01)

(52) U.S. Cl. ........................... 585/478; 585/477

(58) Field of Classification Search .................. 585/478, 585/477
See application file for complete search history.

(56) References Cited

U.S. PATENT DOCUMENTS

| 2,775,628 A | 12/1956 | Nicholson et al. |
| 3,662,013 A | 5/1972 | Machell et al. |
| 3,706,812 A | 12/1972 | Derosset et al. |
| 3,732,325 A | 5/1973 | Pharis et al. |
| 3,773,846 A | 11/1973 | Berger |
| 3,813,452 A | 5/1974 | Bieser |
| 3,939,221 A | 2/1976 | Pearce |

(Continued)

FOREIGN PATENT DOCUMENTS

DE    1910037    10/1969

(Continued)

*Primary Examiner*—Thuan Dinh Dang
(74) *Attorney, Agent, or Firm*—Andrew B. Griffis (57) ABSTRACT

A process for producing a PX-rich product comprises (a) separating a feedstock containing $C_8$ hydrocarbons to produce a $C_8$ hydrocarbons rich stream; (b) separating at least a first portion of the $C_8$ hydrocarbons rich stream to produce a first PX-rich stream and a first PX-depleted stream; (c) isomerizing at least a portion of the first PX-depleted stream to produce a first isomerized stream having a higher PX concentration than the first PX-depleted stream; (d) separating a second portion of the $C_8$ hydrocarbons rich stream and/or at least a portion of the first isomerized stream to produce a second PX-rich stream and a second PX-depleted stream; (e) isomerizing at least a portion of the second PX-depleted stream to produce a second isomerized stream having a higher PX concentration than the second PX-depleted stream; (f) recovering at least a portion of at least one of the first and second PX-rich streams as PX-rich product; and (g) supplying at least a portion of at least one of the first isomerized stream, the second isomerized stream, the first PX-rich stream, and the second PX-rich stream to the separating (a).

20 Claims, 2 Drawing Sheets

U.S. PATENT DOCUMENTS

| | | |
|---|---|---|
| 4,120,911 A | 10/1978 | Davidson |
| 4,188,282 A | 2/1980 | Tabak et al. |
| 4,211,886 A | 7/1980 | Tabak et al. |
| 4,236,996 A | 12/1980 | Tabak et al. |
| 4,886,929 A | 12/1989 | Neuzil et al. |
| 6,004,452 A | 12/1999 | Ash et al. |
| 6,376,733 B1 | 4/2002 | Ferraro et al. |
| 6,376,734 B1 | 4/2002 | Magne-Drisch et al. |
| 6,376,736 B1 | 4/2002 | Rutten et al. |
| 6,600,083 B2 | 7/2003 | Doyle et al. |
| 6,689,929 B2 | 2/2004 | Williams et al. |
| 6,841,714 B2 | 1/2005 | Leflaive et al. |
| 6,878,855 B2 | 4/2005 | Deckman et al. |
| 2005/0167338 A1 | 8/2005 | Miller et al. |
| 2005/0171395 A1 | 8/2005 | Huff, Jr. et al. |

FOREIGN PATENT DOCUMENTS

| | | |
|---|---|---|
| WO | 2005/054161 | 6/2005 |
| WO | 2005/075389 | 8/2005 |
| WO | 2005/075390 | 8/2005 |

PROCESS FOR PRODUCING PARA-XYLENE

CROSS-REFERENCE TO RELATED APPLICATIONS

This application is a continuation of U.S. application Ser. No. 11/784,981, filed Apr. 10, 2007 now U.S. Pat. No. 7,439,412, now allowed, which claims the benefit of U.S. Provisional Application No. 60/794,864, filed Apr. 25, 2006, both hereby incorporated herein by reference.

FIELD OF THE INVENTION

This invention relates to a process for producing para-xylene.

BACKGROUND OF THE INVENTION

Ethylbenzene (EB), para-xylene (PX), ortho-xylene (OX) and meta-xylene (MX) are often present together in $C_8$ aromatic product streams from chemical plants and oil refineries. Of these $C_8$ compounds, although EB is an important raw material for the production of styrene, for a variety of reasons most EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly(ethylene terephthalate), poly(propylene terephthalate), and poly(butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are two major technical challenges in achieving this goal of maximizing PX yield. Firstly, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. Secondly, the $C_8$ aromatics are difficult to separate due to their similar chemical structures and physical properties and identical molecular weights.

A variety of methods are known to increase the concentration of PX in a $C_8$ aromatics stream. These methods normally involve recycling the stream between a separation step, in which at least part of the PX is recovered to produce a PX-depleted stream, and a xylene isomerization step, in which the PX content of the PX-depleted stream is returned back towards equilibrium concentration, typically by contact with a molecular sieve catalyst. However, the commercial utility of these methods depends on the efficiency, cost effectiveness and rapidity of the separation step which, as discussed above, is complicated by the chemical and physical similarity of the different $C_8$ isomers.

Fractional distillation is a commonly used method for separating different components in chemical mixture. However, it is difficult to use conventional fractional distillation technologies to separate EB and the different xylene isomers because the boiling points of the four $C_8$ aromatics fall within a very narrow 8° C. range, namely from about 136° C. to about 144° C. (see Table 1 below). In particular, the boiling points of PX and EB are about 2° C. apart, whereas the boiling points of PX and MX are only about 1° C. apart. As a result, large equipment, significant energy consumption, and/or substantial recycles would be required for fractional distillation to provide effective $C_8$ aromatic separation.

TABLE I

| $C_8$ compound | Boiling Point (° C.) | Freezing Point (° C.) |
|---|---|---|
| EB | 136 | −95 |
| PX | 138 | 13 |
| MX | 139 | −48 |
| OX | 144 | −25 |

Fractional crystallization is an alternative method of separating components of a mixture and takes advantage of the differences between the freezing points and solubilities of the components at different temperatures. Due to its relatively higher freezing point, PX can be separated as a solid from a $C_8$ aromatic stream by fractional crystallization while the other components are recovered in a PX-depleted filtrate. High PX purity, a key property needed for satisfactory conversion of PX to terephthalic acid and terephthalate esters, can be obtained by this type of fractional crystallization. U.S. Pat. No. 4,120,911 provides a description of this method. Commercially available fractional crystallization processes and apparatus include the crystallization isofining process, the continuous countercurrent crystallization process, direct $CO_2$ crystallizer, and scraped drum crystallizers. Due to high utility usage and the formation of a eutectic between PX and MX, it is usually more advantageous to use a feed with as high an initial PX concentration as possible when using fractional crystallization to recover PX.

An alternative xylene separation method uses molecular sieves, such as zeolites, to selectively adsorb para-xylene from the $C_8$ aromatic feedstream to form a PX-depleted effluent. The adsorbed PX can then be desorbed by various ways such as heating, lowering the PX partial pressure or stripping. (See generally U.S. Pat. Nos. 3,706,812, 3,732,325 and 4,886,929) Two commercially available processes used in many chemical plants or refineries are PAREX™ and ELUXYL™ processes. Both processes use molecular sieves to adsorb PX. In such molecular-sieve based adsorption processes, a higher amount of PX, typically over 90%, compared with that from a fractional crystallization process, typically below 65%, may be recovered from the PX present in a particular feed.

For many of these PX separation processes, the higher the original PX concentration in the feed stream, the easier, more efficient and more economical it becomes to perform the PX separation. Therefore, there are strong economic and technical incentives to increase the PX concentration in a hydrocarbon feed stream comprising the $C_8$ aromatic compounds prior to sending the feed stream to a PX recovery unit.

There is, therefore a need for an improved process for increasing the PX concentration in $C_8$ aromatic streams prior to sending the streams to the PX recovery units. This higher PX concentration would also allow better utilization and/or de-bottlenecking of existing PX separation equipment, such as a PAREX™ unit, an ELUXYL™ unit or a fractional crystallizer.

SUMMARY OF THE INVENTION

In one aspect, the present application describes a process for producing a PX-rich product, the process comprising:
  (a) separating a feedstock containing $C_8$ hydrocarbons to produce a $C_8$ hydrocarbons rich stream;
  (b) separating at least a first portion of the $C_8$ hydrocarbons rich stream to produce a first PX-rich stream and a first PX-depleted stream;
  (c) isomerizing at least a portion of the first PX-depleted stream to produce a first isomerized stream having a higher PX concentration than the first PX-depleted stream;
  (d) separating a second portion of the $C_8$ hydrocarbons rich stream and/or at least a portion of the first isomerized stream to produce a second PX-rich stream and a second PX-depleted stream;
  (e) isomerizing at least a portion of the second PX-depleted stream to produce a second isomerized stream having a higher PX concentration than the second PX-depleted stream;
  (f) recovering at least a portion of at least one of the first and second PX-rich streams as PX-rich product; and
  (g) supplying at least a portion of at least one of the first isomerized stream, the second isomerized stream, the first PX-rich stream, and the second PX-rich stream to the separating (a).

Conveniently, the feedstock contains at least $C_8+$ hydrocarbons and the separating (a) produces the $C_8$ hydrocarbons rich stream and a $C_9+$ hydrocarbons rich stream.

In another aspect, the present application describes a process for producing a PX-rich stream, the process comprising:
  (a) separating a feedstock containing $C_8$ hydrocarbons to produce a $C_8$ hydrocarbons rich stream;
  (b) separating at least a portion of the $C_8$ hydrocarbons rich stream to produce the PX-rich stream and a first stream;
  (c) isomerizing at least a portion of the first stream to produce a second stream having a higher PX concentration than the first stream;
  (d) separating at least a portion of the second stream to produce a third stream and a fourth stream, the third stream having a higher PX concentration than the second stream and the fourth stream having a lower PX concentration than the second stream;
  (e) isomerizing at least a portion of the fourth stream to produce a fifth stream having a higher PX concentration than the fourth stream; and
  (f) providing at least a portion of the third stream and/or at least a portion of the fifth stream to the separating step (a).

Additionally, the process may comprise recycling a portion of the fifth stream and/or a portion of the third stream to (d). Further, the process may comprise recycling a portion of the fourth stream to (c).

In one embodiment, the process further comprises fractionating said second stream to produce a first portion rich in $C_7-$ hydrocarbons and a second portion rich in $C_8+$ hydrocarbons, said second portion being supplied to said separating (d).

Conveniently, the separating (b) comprises at least one of selective adsorption, selective crystallization, selective extraction, and selective membrane separation, and the separating (d) comprises at least one of selective adsorption, selective crystallization, selective extraction, and selective membrane separation.

In yet another aspect, the present application describes a process for producing a PX-rich stream, the process comprising:
  (a) separating a feedstock containing $C_8$ hydrocarbons to produce a $C_8$ hydrocarbons rich stream;
  (b) separating at least a portion of the $C_8$ hydrocarbons rich stream to produce a first stream and a second stream, the first stream having a higher PX concentration than the $C_8$ hydrocarbons rich stream and the second stream having a lower PX concentration than the $C_8$ hydrocarbons rich stream;
  (c) isomerizing at least a portion of the second stream to produce a third stream having a higher PX concentration than the second stream;
  (d) separating at least a portion of the first stream and/or at least a portion of the third stream to produce the PX-rich stream and a fourth stream;
  (e) isomerizing at least a portion of the fourth stream to produce a fifth stream having a higher PX concentration than the fourth stream; and
  (f) providing at least a portion of the fifth stream to the separating step (a).

Additionally, the process may comprise recycling at least a portion of the second stream to step (e). Further, the process may comprise recycling at least a portion of the first stream and/or at least a portion of the third stream to step (b).

In one embodiment, the process further comprises fractionating said fifth stream to produce a first portion rich in $C_7-$ hydrocarbons and a second portion rich in $C_8+$ hydrocarbons, said second portion being supplied to said separating (a).

In another embodiment, at least a portion of the third stream is provided to the separating (a).

In this process, the PX-rich stream typically comprises at least 50 wt. % PX, generally at least 90 wt. % PX.

In a further aspect, the present application describes a process for producing a PX-rich product, the process comprising:
  (a) separating a feedstock containing $C_8$ hydrocarbons to produce a $C_8$ hydrocarbons rich stream;
  (b) separating a first portion of the $C_8$ hydrocarbons rich stream to produce a first PX-rich stream and a first stream;
  (c) isomerizing at least a portion of the first stream to produce a second stream having a higher PX concentration than the first stream;
  (d) separating a second portion of the $C_8$ hydrocarbons rich stream to produce a second PX-rich stream and a third stream;
  (e) isomerizing at least a portion of the third stream to produce a fourth stream having a higher PX concentration than the third stream;
  (f) recovering at least a portion of at least one of the first and second PX-rich streams as PX-rich product; and (g) providing at least a portion of the second stream and at least a portion of the fourth stream to the separating (a).

Conveniently, said isomerizing (e) is effected at least partially in the liquid phase.

In one embodiment, the separating (b) comprises selective adsorption and the separating (d) comprises fractional crystallization.

DETAILED DESCRIPTION OF THE INVENTION

All patents, patent applications, test procedures, priority documents, articles, publications, manuals, and other documents cited herein are fully incorporated by reference to the extent such disclosure is not inconsistent with the present application and for all jurisdictions in which such incorporation is permitted.

When numerical lower limits and numerical upper limits are listed herein, ranges from any lower limit to any upper limit are contemplated.

One having ordinary skill in the art understands that the embodiments discussed in this application do not represent all the possible apparatus or process variations embodied by the present disclosure. In addition, many pieces of equipment and apparatus and certain processing steps may be needed for industrial, commercial or even experimental purposes. Examples of such equipments and apparatus and processing steps are, but not limited to, distillation columns, fractionation columns, heat exchanges, pumps, valves, pressure gauges, temperature gauges, liquid-vapor separators, feed and product driers and/or treaters, clay treaters, feed and/or product storage facilities, and processes and steps for process control. While such equipment, apparatus and steps that are not needed for understanding the essence of the present application are not shown in the drawings, some of them may be mentioned from time to time to illustrate various aspects of the disclosure. It is also noted that some of the equipment may be placed at different places in the process depending on the conditions of the processes.

As used herein, the term "$C_8+$ hydrocarbons" means hydrocarbons having eight or more carbon atoms per molecule. A $C_8+$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_8+$ hydrocarbons in the feed and/or product. The term "$C_9+$ hydrocarbons" as used herein means hydrocarbons having nine or more carbon atoms per molecule. A $C_9+$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_9+$ hydrocarbons in the feed and/or product. The term "$C_7-$ hydrocarbons" as used herein means hydrocarbons having seven or less carbon atoms per molecule. A $C_7-$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_7-$ hydrocarbons in the feed and/or product. The term "$C_8$ hydrocarbons" as used herein means hydrocarbons having eight carbon atoms per molecule, including PX. A $C_8$ hydrocarbons feed and/or product, with the exception of a PX-rich or PX-depleted stream and/or product, is a hydrocarbon feed and/or product having more than 10 wt. %, such as more than 20 wt. %, for example more than 40 wt. %, such as more than 50 wt. %, and in some cases more than 80 wt. %, $C_8$ hydrocarbons in the feed and/or product. The term "$C_8$ aromatic hydrocarbons" as used herein means aromatic hydrocarbons having eight carbon atoms per molecule, i.e., xylene(s) and/or EB. A $C_8$ aromatic hydrocarbons feed and/or product, with the exception of a PX-rich or PX-depleted stream and/or product, is a hydrocarbon feed and/or product having more than 10 wt. %, such as more than 20 wt. %, for example more than 40 wt. %, such as more than 50 wt. %, and in some cases more than 80 wt. %, $C_8$ aromatic hydrocarbons in the feed and/or product.

The term "PX-depleted" means that PX concentration in an exiting stream of a particular unit is lowered as compared to the concentration in a feed stream to the same unit. It does not mean that all of PX has to be depleted or removed from the xylenes-containing feed stream(s) to the unit. The term "PX-rich" means that PX concentration in an exiting stream of a particular unit is increased as compared to the concentration in a feed stream to the same unit. It does not mean that the PX concentration has to be 100%.

Feedstock

The feedstock employed in the present process may be any $C_8+$ hydrocarbon feedstock containing $C_8$ aromatic hydrocarbons, such as a reformate stream, a hydrocracking product stream, a xylene or EB reaction product stream, an aromatic alkylation product stream, an aromatic disproportionation stream, an aromatic transalkylation stream, and/or a Cyclar™ process stream. The feedstock may further comprise recycle stream(s) from the isomerization step(s) and/or various separating steps. The $C_8+$ hydrocarbon feedstock comprises PX, together with MX, OX, and/or EB. In addition to xylenes and EB, the $C_8+$ hydrocarbon feedstock may also contain certain amounts of other aromatic or even non-aromatic compounds. Examples of such aromatic compounds are benzene, toluene and $C_9+$ aromatics such as mesitylene, pseudo-cumene and others. These types of feedstream(s) are described in "Handbook of Petroleum Refining Processes", Eds. Robert A. Meyers, McGraw-Hill Book Company, Second Edition, all relevant parts of which are hereby incorporated by reference.

Process Description

The process of the present application comprises an initial separating step that serves to remove the $C_9+$ hydrocarbons from the $C_8+$ hydrocarbon feedstock. Because of the differences in molecular weights, boiling points and other physical and chemical properties, the $C_9+$ hydrocarbons compounds, aromatic or non-aromatic, can be separated relatively easily from the xylenes and EB. Generally, therefore, the first separating step includes fractional distillation, although other separation methods, such as crystallization, adsorption, a reactive separation, a membrane separation, extraction, or any combination thereof, can also be used. These separation methods are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

After removal of the $C_9+$ hydrocarbons, the present process comprises at least one separating step to recover a PX-rich product stream from the resultant $C_8$ hydrocarbon stream. In one embodiment, the PX-rich product stream comprises at least 50 wt. % PX, preferably at least 60 wt. % PX, more preferably at least 70 wt. % PX, even preferably at least 80 wt. % PX, still even preferably at least 90 wt. % PX, and most preferably at least 95 wt. % PX, based on the total weight of the PX-rich product stream. The separating step to recover the PX-rich product stream is performed in a PX recovery unit comprising at least one a crystallization unit, an adsorption unit such as a PAREX™ unit or an ELUXYL™ unit, a reactive separation unit, a membrane separation unit, an extraction unit, a distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

Further separating steps employed in the present process serve to separate a $C_8$ hydrocarbon feedstream into a PX-rich effluent stream and a PX-depleted stream. These separating steps are performed in separating units comprising at least one of a crystallization unit, an adsorption unit such as a PAREX™ unit or an ELUXYL™ unit, a reactive separation unit, a membrane separation unit, an extraction unit, a distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

The process of the present application also comprises at least two isomerization steps, in each of which a feed stream comprising $C_8$ aromatic compounds is isomerized to produce an isomerization effluent. The feed stream to each isomerization step comprises PX in a concentration below its equilibrium concentration relative to other inter-convertible $C_8$ aromatic compounds under the isomerization conditions. Each catalyzed isomerization step serves to increase the PX concentration to near its equilibrium level. The isomerization step may also serve to convert part or all of EB present in the feed stream to benzene and light hydrocarbons (i.e., hydrocarbons having less than 6 carbons per molecule). Alternatively, the isomerization step may also serve to isomerize part or all of EB present in the feed stream to xylene(s).

There are many catalysts or combinations of catalysts that can be used in each isomerization step to effect the desired reaction. There are generally two types of xylene isomerization catalysts. One type of isomerization catalyst can more or less equilibrate the four different $C_8$ aromatic compounds, including EB, to the concentrations dictated by thermodynamics under the reaction conditions. This allows maximum formation of PX from $C_8$ aromatics in a particular feed. Examples of these type catalysts include IFP/Engelhard Octafining™ and Octafining II™ catalysts used in the respective processes. The other type of xylene isomerization catalyst can effect EB conversion in addition to xylene isomerization, generally in the presence of hydrogen. As discussed earlier, this type of catalyst will remove EB and produce benzene and ethane as byproducts. This may be a desirable disposition of EB, depending on supplies and demands of various products as well as other equipment present in a particular plant. Examples include Mobil High Temperature Isomerization (MHTI™) catalysts, Mobil High Activity Isomerization catalysts (MHAI™) and UOP ISOMAR™ I-100 catalysts.

A number of suitable isomerization reactors may be used for the present disclosure. Some non-limiting examples are described in U.S. Pat. Nos. 4,899,011 and 4,236,996.

For the present disclosure, a xylene isomerization reaction may be carried out in a liquid phase, a vapor (gas) phase, a super critical phase, or a combination thereof. The selection of isomerization reaction conditions and the specific composition of the aromatic feed stream being isomerized determine the physical state of the aromatic feed stream in the xylene isomerization reactor.

Figure 1:
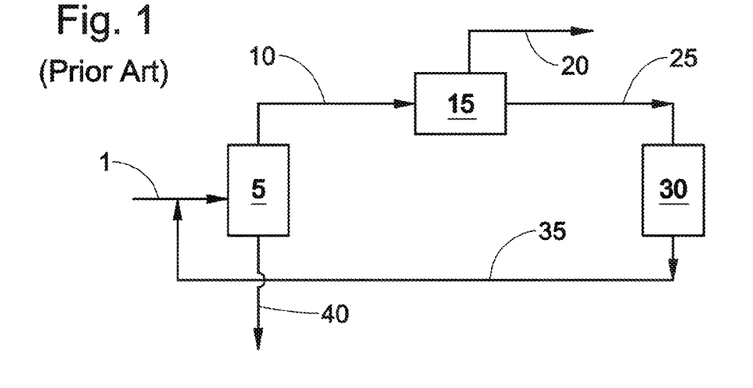
FIG. 1 is a schematic diagram of a conventional xylene separation and isomerization loop.

Referring to FIG. 1, in the conventional para-xylene separation and isomerization loop shown, a feed comprising $C_8$+ aromatic hydrocarbons is directed via line 1 to a separation unit 5, which is typically a distillation column. A majority of $C_8$ aromatic hydrocarbons in the feed is separated by the unit 5 and withdrawn via a line 10, while a majority of $C_9$+ hydrocarbons in the feed is withdrawn via a line 40 as a bottom stream for further processing. The $C_8$ aromatic hydrocarbons stream withdrawn via line 10 is supplied to a PX recovery unit 15 where a portion of PX in the stream is removed via line 20. The PX depleted effluent from the PX recovery unit 15 is withdrawn via a line 25 and is supplied to an isomerization unit 30. The isomerization unit 30 is normally a reactor or a vessel loaded with an isomerization catalyst (e.g., acidic zeolite) and operated under suitable isomerization conditions sufficient to convert the PX depleted stream into an isomerized stream having a higher PX concentration than the PX concentration of the PX depleted stream. The isomerized stream is withdrawn from the isomerization unit 30 and recycled to the separation unit 5 via line 35.

Figure 2:
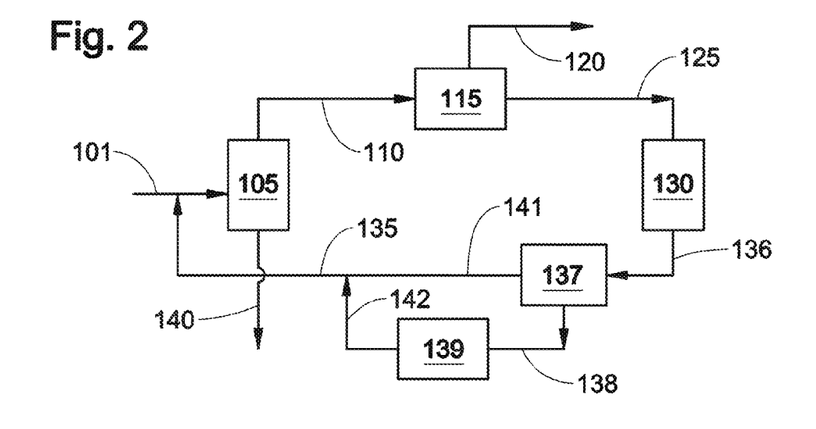
FIG. 2 is a schematic diagram of a process for producing para-xylene in accordance with a first embodiment of this disclosure.

Referring to FIG. 2 which describes one embodiment of the present process, a feedstock comprising $C_8$+ aromatic hydrocarbons is directed via line 101 to a first separation unit 105. The first separation unit 105 may be any unit capable of separating $C_8$ aromatic hydrocarbons from a feedstock comprising $C_8$+ aromatic hydrocarbons and typically is a distillation column. A majority of $C_8$ aromatic hydrocarbons in the feedstock is separated by the unit 105 and withdrawn via a line 110, while a majority of $C_9$+ hydrocarbons in the feed is withdrawn via a line 140 as a bottom stream for further processing. At least a portion of the $C_8$ aromatic hydrocarbon stream withdrawn via line 110 is supplied to a PX recovery unit 115 where a portion of PX in the feed is withdrawn as a PX-rich stream via a line 120 and a first stream (PX depleted stream) is withdrawn via a line 125.

At least a portion of the first stream withdrawn from the PX recovery unit 115 via line 125 is supplied to a first isomerization unit 130. The first isomerization unit 130 is normally a reactor loaded with an isomerization catalyst (e.g., acidic zeolite) and is operated under suitable isomerization conditions sufficient to convert the first stream into a second stream having a higher PX concentration than the PX concentration of the first stream. The second stream is withdrawn from the first isomerization unit 130 and at least a portion thereof is supplied via line 136 to a second separation unit 137, where the second stream supplied is separated into a third stream, having a higher PX concentration than the second stream, and a fourth stream, having a lower PX concentration than the second stream.

The fourth stream is withdrawn from the second separation unit 137 via line 138 and at least a portion thereof is supplied to a second isomerization unit 139. The second isomerization unit 139 is normally a reactor or a vessel loaded with an isomerization catalyst (e.g., acidic zeolite) and operated under suitable isomerization conditions sufficient to convert the fourth stream into a fifth stream having a higher PX concentration than the PX concentration of the fourth stream.

The fifth stream is withdrawn from the second isomerization unit 139 via line 142 and is combined with the third stream, which is withdrawn from the second separation unit 137 via line 141. At least a portion of the fifth stream and/or at least a portion of the third stream are jointly fed to the first separation unit 105 via line 135.

In a modification (not shown) of the process of FIG. 2, a portion of the fifth stream in line 142 and/or a portion of the third stream in line 141 may be recycled to the second separation unit 137. Further, the process may comprise recycling at least a portion of the fourth stream in line 138 to the first isomerization unit 130.

In a further modification (not shown) of the process of FIG. 2, the second stream withdrawn from the first isomerization unit 130 via line 136 is fed to a fractionator before being supplied to the second separation unit 137. The fractionator divides the second stream into a first portion rich in $C_7-$ hydrocarbons, which is withdrawn for further processing, and a second portion rich in $C_8+$ hydrocarbons, which is supplied to the second separation unit 137.

Figure 3:
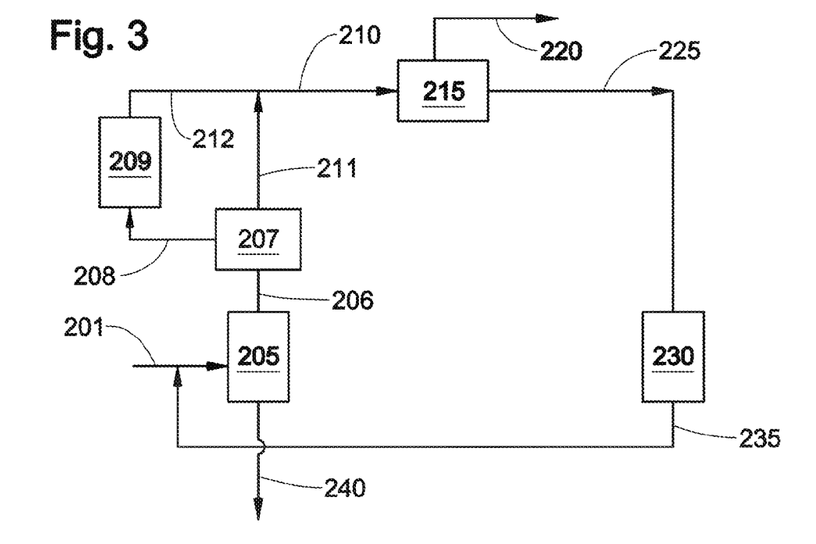
FIG. 3 is a schematic diagram of a process for producing para-xylene in accordance with a second embodiment of this disclosure.

Referring to FIG. 3, which describes another embodiment of the present process, a feedstock comprising $C_8+$ aromatic hydrocarbons is directed via line 201 to a first separation unit 205. The first separation unit 205 may be any unit capable of separating $C_8$ aromatic hydrocarbons from a feedstock comprising $C_8$ and $C_9+$ aromatic hydrocarbons, again normally a distillation column. A majority of $C_8$ aromatic hydrocarbons in the feedstock is separated by the unit 205 and withdrawn via a line 206, while a majority of $C_9+$ hydrocarbons in the feed is withdrawn via a line 240 as a bottom stream for further processing. At least a portion of the $C_8$ aromatic hydrocarbon stream withdrawn via line 206 is supplied to a second separation unit 207, which may be any unit capable of separating or enriching PX from a feedstock comprising $C_8$ aromatic hydrocarbons.

The second separation unit 207 separates a portion of the $C_8$ aromatic hydrocarbon stream withdrawn a line 206 into a first stream, having a higher PX concentration than the $C_8$ aromatic hydrocarbon stream and a second stream, having a lower PX concentration than the $C_8$ aromatic hydrocarbon stream. The second stream is withdrawn from the first separation unit 207 via line 208 and at least a portion thereof is supplied to a first isomerization unit 209. The first isomerization unit 209 is normally a reactor loaded with an isomerization catalyst (e.g., acidic zeolite) and operated under suitable isomerization conditions sufficient to convert second stream into a third stream having higher PX concentration than the PX concentration of the second stream. The third stream is withdrawn from the first isomerization unit 209 via line 212 and is combined with the first stream, which is withdrawn from the second separation unit 207 via line 211.

At least a portion of the third stream and/or at least a portion of the first stream are jointly fed via line 210 to a PX recovery unit 215 where a portion of PX in the joint stream is removed via line 220 as a PX-rich stream and a fourth stream (PX depleted stream) is withdrawn via a line 225. At least a portion of the fourth stream is supplied via line 225 to a second isomerization unit 230. The second isomerization unit 230 is normally a reactor loaded with an isomerization catalyst (e.g., acidic zeolite) and operated under suitable isomerization conditions sufficient to convert the fourth stream into a fifth stream having higher PX concentration than the PX concentration of the fourth stream. The fifth stream is withdrawn from the second isomerization unit 230 and at least a portion thereof is supplied to the first separation unit 205 via line 235.

In a modification (not shown) of the process of FIG. 3, a portion of the second stream in line 208 may be supplied to the second separation unit 230. In addition, a portion of the first stream in line 211 and/or a portion of the third stream in line 212 may be recycled to the second separation unit 207.

In a further modification (not shown) of the process of FIG. 3, at least a portion of the third stream in line 212 may be supplied to the first separation unit 205.

In yet a further modification (not shown) of the process of FIG. 3, the fifth stream withdrawn from the second isomerization unit 230 via line 235 is fed to a fractionator before being supplied to the first separation unit 207. The fractionator divides the fifth stream into a first portion rich in $C_7-$ hydrocarbons, which is withdrawn for further processing, and a second portion rich in $C_8+$ hydrocarbons, which is supplied to the second separation unit 207.

Figure 4:
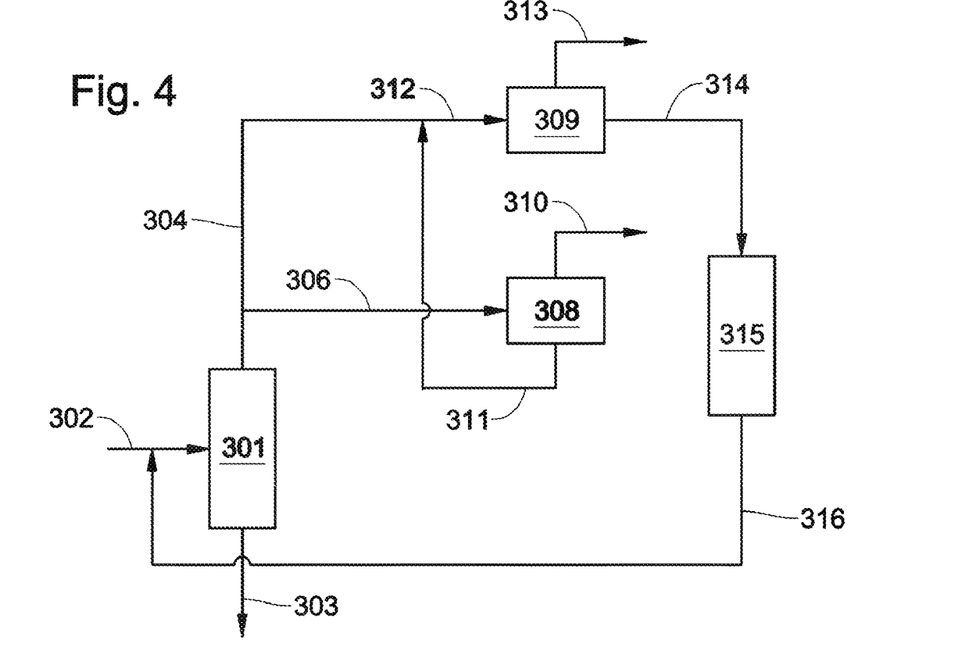
FIG. 4 is a schematic diagram of a further conventional xylene separation and isomerization loop.

Referring now to FIG. 4, a further known xylene production process is shown that integrates selective adsorption and a fractional crystallization unit in a single para-xylene separation and isomerization loop. In particular, the process comprises a comprises a first separating unit 301, which may be one or more distillation columns and which receives a $C_8+$ aromatic hydrocarbon feed stream from line 302 and separates the feed into an overhead vapor stream and a bottom liquid stream. The bottom liquid stream is composed mainly of $C_9+$ aromatic hydrocarbons and some ortho-xylene (OX) and is removed from the first separating unit 301 through line 303 for further processing. The overhead stream is composed mainly of $C_8$ aromatic hydrocarbons (typically about 50% meta xylene (MX), about 20% PX, about 15% OX and about 15% EB) and is removed from the first separating unit 301 through line 304 and is sent for PX recovery.

PX recovery in the process shown in FIG. 4 is effected by both a fractional crystallization unit 308 and a selective adsorption unit 309. Thus part of the $C_8$ aromatic hydrocarbon removed from the first separating unit 301 through line 304 is fed by line 306 to the fractional crystallization unit 308, where a first PX-rich product stream is recovered through line 310 and a PX-depleted raffinate stream is withdrawn via line 311. The remainder of the $C_8$ aromatic hydrocarbon removed from the first separating unit 301 through line 304 is combined with the PX-depleted raffinate stream from the fractional crystallization unit 308 and fed by line 312 to the selective adsorption unit 309, where a second PX-rich product stream is recovered through line 313 and a further PX-depleted stream is withdrawn via line 314. The further PX-depleted stream is fed by line 314 to a xylene isomerization unit 315 where the further stream is converted into an isomerized stream having higher PX concentration than that of the further stream. The isomerized stream is removed from the xylene isomerization unit 315 by line 316 and is fed to line 302 for recycle to the splitter 301.

Figure 5:
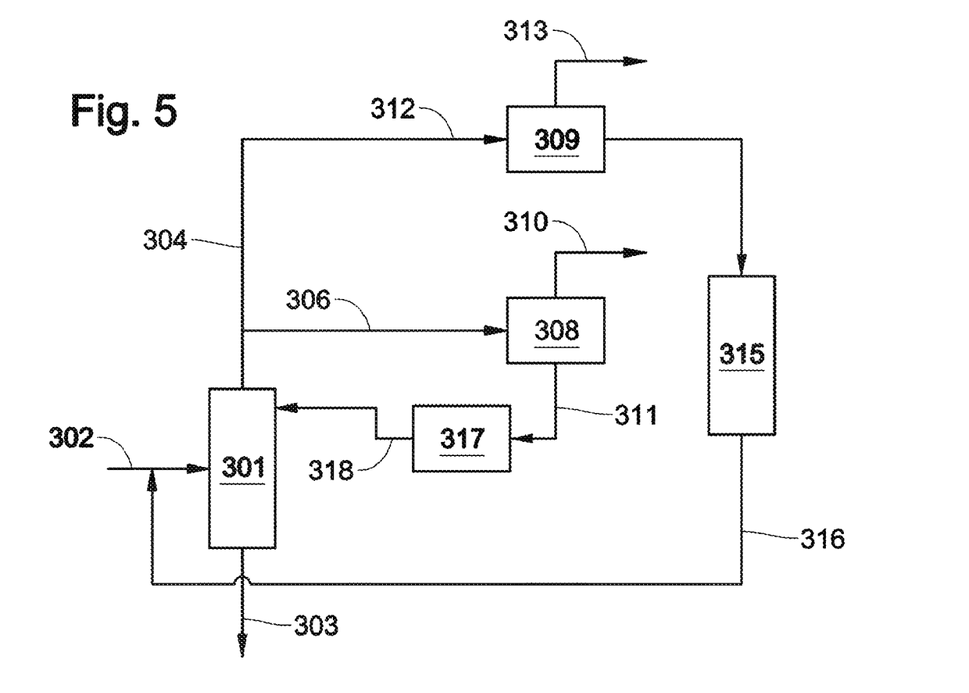
FIG. 5 is a schematic diagram of a process for producing para-xylene in accordance with a third embodiment of this disclosure.

Referring to FIG. 5, a modification of the known technology of FIG. 4 is shown in which the present process is used to increase the PX productivity of the para-xylene separation and isomerization loop. Like reference numerals are therefore used to illustrate like components in FIGS. 4 and 5. In particular the process of Example 5 employs a second xylene isomerization unit 317 which is used to treat the PX-depleted raffinate stream withdrawn from the fractional crystallization unit 308 via line 311. Thus a problem with the known process shown in FIG. 4 is the low PX concentration in the crystallizer raffinate stream, which reduces the productivity of the selective adsorption unit 309 since, in each pass, the unit 309 can only recover the PX being fed through line 312. The purpose of the treatment in the second xylene isomerization unit 316 is to bring the PX concentration in the PX-depleted raffinate stream from 10-12% up to the equilibrium level of 20-24%.

In the process shown in FIG. 5, the effluent stream from the second xylene isomerization unit 317, which has a higher PX concentration than the PX-depleted raffinate stream, is withdrawn through line 318 and fed to the first separating unit 301. In this way, the overall PX content of the feed to the selective adsorption unit 309 can be increased. It is, however, to be appreciated that part or all of the effluent stream from second xylene isomerization unit 317 could be supplied directly to the selective adsorption unit 309, if necessary after fractionation to remove $C_9+$ hydrocarbon impurities and/or $C_7-$ hydrocarbon impurities generated in the second xylene isomerization unit 317.

In one practical embodiment of the process shown in FIG. 5, the second xylene isomerization unit 316 employs liquid phase isomerization technology since this has the advantages of (1) simplicity and cost, since, unlike the more common, gas phase, high temperature isomerization technologies, liquid phase isomerization does not require hydrogen recycle; and (2) low xylene loss (<1.0%) due to the low levels of undesirable side reactions at the more moderate reaction conditions.

Because the liquid isomerization product contains mostly equilibrium xylenes and low levels of C9+ compounds, it is possible to send the effluent stream from the second xylene isomerization unit 317 directly to the first separating unit 301 at the proper tray position to affect the separation of C8 and C9+ compounds.

EXAMPLES

The following simulation examples were performed based on the following assumptions:
(a) the isomerization unit(s) isomerizes PX, MX, and OX to their thermodynamic equilibrium;
(b) the equilibrium PX concentration in xylenes (excluding EB) is 25%;
(c) the isomerization unit(s) converts all EB to benzene, toluene, xylenes, or other hydrocarbons;
(d) the PX recovery unit recovers 100% of PX in its feed; and
(e) the first separation unit is a distillation column which recovers all xylenes in the combined feed.

It is understood to a person skilled in the art that the isomerization unit(s) may isomerize PX, MX, and OX to less than 100% thermodynamic equilibrium concentration in real manufacturing plants. It is also understood to a person skilled in the art that the PX equilibrium concentration in xylenes (excluding EB) is usually less than 25%. It is again understood to a person skilled in the art that the isomerization unit(s) may convert less than 100% EB to other hydrocarbons. It is further understood to a person skilled in the art that the PX recovery unit may recover less than 100% of PX in its feed in real manufacturing plants. However, for the purpose of simplicity, 100% xylene equilibrium, 100% EB conversion, 100% PX recovery, and 25% PX equilibrium concentration are assumed in the following Examples.

Comparative Example 1

As shown in the simplified schematic diagram of a conventional process for producing PX in FIG. 1, one unit of xylenes in a $C_8+$ aromatic feedstock (via line 1) is combined with a recycle stream (via line 35) having 3 units of xylenes and is directed to the separation unit 5 (distillation column). The majority of $C_9+$ hydrocarbons are separated from the combined feed by the distillation column 5 and withdrawn via line 40 as a bottom stream for further processing. The overhead stream from the distillation column 5 contains the majority of $C_8$ aromatic hydrocarbons (xylenes and EB) in the feed and has four units of total xylenes, of which 25% (1 unit) is PX. The overhead stream is withdrawn via line 10 and supplied to the PX recovery unit 15 via line 10. The PX recovery unit used in this example is a PAREX™ unit. One unit of the PX in the overhead stream is removed via line 20 as a PX-rich stream having a PX concentration of about 99.6 to 99.9 wt. % PX based on the total weight of the PX-rich stream. A PX depleted stream is withdrawn recovery unit 15 via line 25 and fed to the isomerization unit 30. In this example, the isomerization unit isomerizes MX and OX to PX; and converts EB to mainly benzene and other hydrocarbons. The isomerized stream having about 3 units of xylenes and a PX concentration (among total xylenes) of about 25 wt. % is withdrawn from the isomerization unit 30 and recycled back to the separation unit 5 via line 35.

Example 1

As shown in the simplified schematic diagram of one embodiment of this disclosure (FIG. 2), one unit of xylenes in a $C_8+$ aromatic feedstock is combined with a recycle stream having 2 units of xylenes and is directed via line 1 to the first separation unit 105 (distillation column). The majority of $C_9+$ hydrocarbons are separated from the combined feed by the distillation column 105 and withdrawn via line 140 as a bottom stream for further processing. The overhead stream of the distillation column 105 contains the majority of $C_8$ aromatic hydrocarbons (xylenes and EB) in the feed and has 3 units of total xylenes, of which about 33.3% are PX. The overhead stream is withdrawn via line 110 and supplied to the PX recovery unit 115, which in this example is a PAREX™ unit. One unit of the PX in the overhead stream is removed via line 120 as a PX-rich stream having a PX concentration of about 99.6 to 99.9 wt. % based on the total weight of the PX-rich stream. A PX depleted stream is withdrawn from unit 115 via line 125 and fed to the first isomerization unit 130. In this example, the first isomerization unit isomerizes MX and OX to PX; and converts EB to mainly benzene and other hydrocarbons. The isomerized stream from the first isomerization unit 130 having about 2 unit of xylenes and a PX concentration (among total xylenes) of about 25 wt. % is withdrawn from the isomerization unit 130.

The isomerized stream from the first isomerization unit 130 is supplied via line 136 to the second separation unit 137 and separated into a stream having a higher PX concentration than the isomerized stream from the first isomerization unit 130 and a stream having a lower PX concentration than the isomerized stream from the first isomerization unit 130. The stream having a lower PX concentration than the isomerized stream from the first isomerization unit 130 is withdrawn from the second separation unit 137 via line 138 and supplied to the second isomerization unit 139. The product stream from the second isomerization unit 139 is withdrawn via line 142 and combined with the stream having a higher PX concentration than the isomerized stream from the first isomerization unit 130 to form a combined product withdrawn via line 135. The second isomerization unit 139 and the second separation unit 137 are operated so that the combined product (in line 135) has a PX concentration of about 37% among total xylenes. The combined product is recycled back to the separation unit 105 via line 135.

It will be seen that the ratio of the recycle stream (combined product via line 135) to the feed stream (via line 101) in Example 1 is 2:1, down from the 3:1 recycle ratio in Comparative Example 1, which debottlenecks the existing xylene loop.

Example 2

As show in the simplified schematic diagram of one embodiment of this disclosure (FIG. 3), one unit of xylenes in a $C_8+$ aromatic feedstock fed via line 201 is combined with a recycle stream having 2 units of xylenes fed via line 235 and is directed to the first separation unit 205 (distillation column). The majority of $C_9+$ hydrocarbons in the feed are separated in the distillation column 205 and withdrawn via line 240 as a bottom stream for further processing. The overhead stream from the distillation column contains the majority of $C_8$ aromatic hydrocarbons (xylenes and EB) in the feed and has 3 units of total xylenes. The overhead stream is withdrawn from the distillation column via line 206 and supplied to the second separation unit 207 here the overhead stream is separated into a stream having a higher PX concentration than the overhead stream in line 211 and a stream having a lower PX concentration than the overhead stream in line 208. The lower PX concentration stream in line 208 is supplied to the first isomerization unit 209 and is isomerized to produce an effluent stream which is combined with the higher PX concentration stream in line 211. The first isomerization unit 209 and the second separation unit 207 are operated so that the combined product (in line 210) has a PX concentration of about 33.3% based on total xylenes.

The combined product in line 210 is supplied to the PX recovery unit 215, which in this example is a PAREX™ unit. One unit of the PX in the overhead stream is removed via line 220 as a PX-rich stream, which has a PX concentration of about 99.6 to 99.9 wt. % PX based on the total weight of the PX-rich stream. A PX depleted stream is withdrawn from the PX recovery unit 215 via a line 225 and enters the second isomerization unit 230. In this example, the second isomerization unit isomerizes MX and OX to PX; and converts EB to mainly benzene and other hydrocarbons. The isomerized stream from the second isomerization unit 230 has about 2 unit of xylenes and a PX concentration (among total xylenes) of about 25 wt. % and is recycled back to the separation unit 205 via line 135.

Again it will be seen that the ratio of the recycle stream (via line 235) to the feed stream (via line 201) in Example 1 is 2:1, down from the 3:1 recycle ratio in Comparative Example 1, which debottlenecks the existing xylene loop.

The arrangements in Examples 1 and 2 reduce the recycle/feed ratio to 2. Assuming an original capacity of 4 units of xylenes in the xylene loop and assuming this capacity is fully utilized, a 1.33 unit of feed and a 2.66 unit recycle satisfy the recycle-to-feed ratio of 2 and completely fill up the original capacity of 4 units of feed to the PX recovery unit. A total 1.33 units of PX is recovered from the PX recovery unit compared to the one (1) unit of feed in the conventional PX plant as shown in the Comparative Example, thereby demonstrating a 33% increase in PX production capacity (1.33 from 1.0).

Comparative Example 2

In the simulation of the known process shown in FIG. 4, it is assumed that 1.2 units of xylenes in a $C_8+$ aromatic feedstock fed via line 302 are combined with a recycle stream fed having 4.3 units of xylenes fed via line 316 to give a total xylenes feed to the first separating unit 301 of 5.5 units of which 2.4 units of the overhead stream are sent to the selective adsorption unit 309 and 3.1 units are sent to the fractional crystallization unit 308 via line 306. The fractional crystallization unit 308 separates 0.4 units of high purity PX (>99.5%) from the condensed liquid in the line 306 leaving 2.7 units of PX-depleted raffinate, which contains 10-12% PX and mostly other xylene isomers.

The 2.7 units of the PX-depleted raffinate from fractional crystallization unit 308 are combined with the remaining 2.4 units of condensed liquid from the condenser 305 to give a total feed of 5.1 units to the selective adsorption unit 309. Because the PX-depleted raffinate has only 10-12% PX, the mixture, which is sent to selective adsorption unit 309, typically has a PX concentration of about 15-18%. The selective adsorption unit 309 in this Example is a PAREX unit and produces 0.8 units of high purity PX (>99.5%) and 4.3 units of a further PX-depleted raffinate stream. The further PX-depleted raffinate stream is supplied to the xylene isomerization unit 315 which generates 4.3 units of xylenes at 24-25% PX concentration, which is recycled back to the splitter 301.

Example 3

In the simulation of the process shown in FIG. 5, the total xylenes feed to the first separating unit 301 remains at 5.5 units but is composed of 1.4 units of xylenes in the $C_8+$ aromatic feedstock fed via line 302 and 4.1 units of xylenes in the recycle stream fed via line 316. The overhead stream from the first separating unit 301 again comprises 5.5 units of xylenes. As in the case of Comparative Example 2, 3.1 units of the overhead stream are sent to the fractional crystallization unit 308, where 0.4 units of high purity PX (>99.5%) are recovered leaving 2.7 units of PX-depleted raffinate. However, in Example 3, the PX-depleted raffinate is fed to the liquid phase isomerization reactor 317, which increases the PX concentration of the raffinate to about 23 wt %. The resultant 2.7 units of isomerized raffinate are recycled to the first separating unit 301. The overhead stream in line 304 therefore has a total of 8.2 units (5.5 units+2.7 units), of which 5.1 units are supplied via line 312 to the PAREX unit 309, but in this case the PX concentration of the feed to the PAREX unit is 20-24 wt % (as compared with the 15-18 wt % of Comparative Example 2), which effectively allows a 25% PAREX productivity increase from 0.8 units to 1.0 units of PX. As a result, the PAREX raffinate stream in line 314 is reduced from 4.3 units to 4.1 units saving energy as the amount of recycle is reduced. The fresh feed has increased from 1.2 units to 1.4 units to meet the new capacity. However, the total quantity of molecules going into the first separating unit 301 (5.5 units), the crystallizer (3.1 units), and the PAREX unit (5.1 units) all remain unchanged. Thus, the proposed technology debottlenecks the whole loop with a minimum amount of new equipment.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a PX-rich product, the process comprising:
   (a) separating a feedstock containing $C_8$ hydrocarbons to produce a $C_8$ hydrocarbons rich stream;
   (b) separating at least a first portion of the $C_8$ hydrocarbons rich stream to produce a first PX-rich stream and a first PX-depleted stream;
   (c) isomerizing at least a portion of the first PX-depleted stream to produce a first isomerized stream having a higher PX concentration than the first PX-depleted stream;
   (d) separating a second portion of the $C_8$ hydrocarbons rich stream or at least a portion of the first isomerized stream to produce a second PX-rich stream and a second PX-depleted stream;
   (e) isomerizing at least a portion of the second PX-depleted stream to produce a second isomerized stream having a higher PX concentration than the second PX-depleted stream;
   (f) recovering at least a portion of at least one of the first and second PX-rich streams as PX-rich product; and
   (g) supplying at least a portion of at least one of the first isomerized stream, the second isomerized stream, the first PX-rich stream, and the second PX-rich stream to the separating (a).

2. The process recited in claim 1, wherein the feedstock contains at least $C_8+$ hydrocarbons and the separating (a) produces the $C_8$ hydrocarbons rich stream and a $C_9+$ hydrocarbons rich stream.

3. The process recited in claim 1, wherein each PX-rich stream comprises at least 90 wt. % PX.

4. The process recited in claim 1, wherein said separating (b) and said separating (d) are each independently selected from at least one of selective adsorption, selective crystallization, selective extraction, and selective membrane separation.

5. The process recited in claim 1, wherein at least one of said isomerizing (c) and said isomerizing (e) is carried out in an isomerization unit containing a catalyst operated under isomerization conditions sufficient to isomerize MX and/or OX to PX and/or to convert EB to benzene and/or xylenes.

6. A process for producing a PX-rich stream, comprising the steps of:
   (a) separating a feedstock containing $C_8$ hydrocarbons to produce a $C_8$ hydrocarbons rich stream;
   (b) separating at least a portion of said $C_8$ hydrocarbons rich stream to produce said PX-rich stream and a first stream;
   (c) isomerizing at least a portion of said first stream to produce a second stream having a higher PX concentration than said first stream;
   (d) separating at least a portion of said second stream to produce a third stream and a fourth stream, said third stream having a higher PX concentration than said second stream and said fourth stream having a lower PX concentration than said second stream;
   (e) isomerizing at least a portion of said fourth stream in another isomerizing step separated from said isomerization step (c) to produce a fifth stream having a higher PX concentration than said fourth stream; and
   (f) providing at least a portion of said third stream or at least a portion of said fifth stream to said separating step (a).

7. The process recited in claim 6, and further comprising recycling at least a portion of said fifth stream and/or at least a portion of said third stream to step (d).

8. The process recited in claim 6, and further comprising recycling at least a portion of said fourth stream to step (c).

9. The process recited in claim 6, and further comprising fractionating said second stream to produce a first portion rich in $C_7-$ hydrocarbons and a second portion rich in $C_8+$ hydrocarbons, said second portion being supplied to said separating (d).

10. The process recited in claim 6, wherein said PX-rich stream comprises at least 90 wt. % PX.

11. A process for producing a PX-rich stream, comprising the steps of:
   (a) separating a feedstock containing $C_8$ hydrocarbons to produce a $C_8$ hydrocarbons rich stream;
   (b) separating at least a portion of said $C_8$ hydrocarbons rich stream to produce a first stream and a second stream, said first stream having a higher PX concentration than said $C_8$ hydrocarbons rich stream and said second stream having a lower PX concentration than said $C_8$ hydrocarbons rich stream;
   (c) isomerizing at least a portion of said second stream to produce a third stream having a higher PX concentration than said second stream;
   (d) separating at least a portion of said first stream or at least a portion of said third stream to produce said PX-rich stream and a fourth stream;
   (e) isomerizing at least a portion of said fourth stream to produce a fifth stream having a higher PX concentration than said fourth stream; and
   (f) providing at least a portion of said fifth stream to said separating step (a).

12. The process recited in claim 11, and further comprising at least one of recycling at least a portion of said second stream to step (e), recycling at least a portion of said first stream to step (b), and recycling at least a portion of said third stream to step (b).

13. The process recited in claim 11, and further comprising fractionating said fifth stream to produce a first portion rich in $C_7-$ hydrocarbons and a second portion rich in $C_8+$ hydrocarbons, said second portion being supplied to said separating (a).

14. The process recited in claim 11, wherein said PX-rich stream comprises at least 90 wt. % PX.

15. A process for producing a PX-rich product, the process comprising:
   (a) separating a feedstock containing $C_8$ hydrocarbons to produce a $C_8$ hydrocarbons rich stream;
   (b) separating a first portion of the $C_8$ hydrocarbons rich stream to produce a first PX-rich stream and a first stream;

(c) isomerizing at least a portion of the first stream to produce a second stream having a higher PX concentration than the first stream;

(d) separating a second portion of the $C_8$ hydrocarbons rich stream to produce a second PX-rich stream and a third stream;

(e) isomerizing at least a portion of the third stream to produce a fourth stream having a higher PX concentration than the third stream;

(f) recovering at least a portion of the first or second PX-rich streams as PX-rich product; and (g) providing at least a portion of the second stream and at least a portion of the fourth stream to the separating (a).

16. The process recited in claim 15, wherein said isomerizing (e) is carried out in an isomerization unit containing a catalyst operated under isomerization conditions sufficient to isomerize MX and/or OX to PX and/or to convert EB to benzene and/or xylenes.

17. The process recited in claim 15, wherein said isomerizing (e) is carried out in an isomerization unit containing a catalyst operated under isomerization conditions sufficient to isomerize MX and/or OX to PX and/or to convert EB to benzene and/or xylenes.

18. The process recited in claim 15, wherein said isomerizing (e) is effected at least partially in the liquid phase.

19. The process recited in claim 15, wherein said separating (b) comprises selective adsorption.

20. The process recited in claim 15, wherein said separating (d) comprises fractional crystallization.

* * * * *